(12) United States Patent
Bakker et al.

(10) Patent No.: US 7,678,252 B2
(45) Date of Patent: Mar. 16, 2010

(54) LONG LIVED ANION-SELECTIVE SENSORS BASED ON A COVALENTLY ATTACHED METALLOPORPHYRIN AS ANION RECEPTOR

(75) Inventors: Eric Bakker, West Lafayette, IN (US); Yu Qin, Beijing (CN)

(73) Assignee: Auburn University, Auburn, AL (US)

( * ) Notice: Subject to any disclaimer, the term of this patent is extended or adjusted under 35 U.S.C. 154(b) by 556 days.

(21) Appl. No.: 11/424,185

(22) Filed: Jun. 14, 2006

(65) Prior Publication Data

US 2006/0278526 A1 Dec. 14, 2006

Related U.S. Application Data

(60) Provisional application No. 60/690,247, filed on Jun. 14, 2005.

(51) Int. Cl.
  *G01N 27/26* (2006.01)
(52) U.S. Cl. .................. 204/418; 424/450; 600/317; 604/20
(58) Field of Classification Search ........... 525/63–87; 204/418; 424/450; 604/20; 600/317
See application file for complete search history.

(56) References Cited

U.S. PATENT DOCUMENTS

| | | | |
|---|---|---|---|
| 3,756,827 A | | 9/1973 | Chang |
| RE27,925 E | | 2/1974 | Jenkins et al. |
| 4,320,940 A | | 3/1982 | Mueller et al. |
| 4,526,945 A | * | 7/1985 | Carlson et al. ............ 526/145 |
| 4,680,354 A | * | 7/1987 | Lin et al. ............ 526/172 |
| 4,762,799 A | | 8/1988 | Seitz et al. |
| 5,096,799 A | | 3/1992 | Fujikura et al. |
| 6,002,954 A | * | 12/1999 | Van Antwerp et al. ...... 600/317 |
| 6,060,327 A | * | 5/2000 | Keen ............................ 506/9 |
| 6,143,570 A | | 11/2000 | Alder et al. |
| 6,242,158 B1 | | 6/2001 | Kosaka et al. |
| 6,974,618 B2 | | 12/2005 | Kumacheva et al. |
| 7,201,876 B2 | | 4/2007 | Peper et al. |
| 7,226,563 B2 | | 6/2007 | Bakker et al. |
| 2003/0148142 A1 | * | 8/2003 | Fryd et al. ................. 428/690 |
| 2003/0187104 A1 | * | 10/2003 | Guilbault et al. ............. 524/59 |
| 2003/0213691 A1 | | 11/2003 | Peper et al. |

(Continued)

FOREIGN PATENT DOCUMENTS

WO WO-2007/146615 A2 * 12/2007

OTHER PUBLICATIONS

Kibbey, C.E. et al., "Further studies on the potentiometric salicylate response of polymeric membranes doped with tin(IV)-tetraphenylporphyrins," J. Electroanal. Chem., (1992), pp. 135-149, vol. 335.

(Continued)

*Primary Examiner*—Peter D. Mulcahy
*Assistant Examiner*—Henry Hu
(74) *Attorney, Agent, or Firm*—Haverstock & Owens LLP

(57) ABSTRACT

A graft copolymer having metalloporphyrin ionophores covalently attached in a manner that prevents dimer formation is provided. A method of making the graft copolymer comprises polymerizing a functionalized metalloporphyrin monomer, which includes a polymerizable group, with a co-monomer. Methods for synthesizing the polymerizable metalloporphyrin monomers are provided. The graft copolymer can be incorporated into anion-selective membranes for use in anion-detecting sensors, which have improved longevity and response times.

17 Claims, 6 Drawing Sheets

U.S. PATENT DOCUMENTS

2003/0217920 A1    11/2003    Peper et al.
2004/0058384 A1    3/2004    Bakker et al.
2005/0011760 A1    1/2005    Bakker et al.

OTHER PUBLICATIONS

Li, X. et al., "Measurement of Concentration Profiles inside a Nitrite Ion Selective Electrode Membrane," Anal. Chem., (1991), pp. 2168-2174, vol. 63.

Malinowska, E. et al., "Novel approach of immobilization of calix[4]arene type ionophore in 'self-plasticized' polymeric membrane," Analytica Chimica Acta, (2000), pp. 93-101, vol. 421.

Malinowska, E. et al., "Potentiometric and spectroscopic characterization of anion selective electrodes based on metal(III) porphyrin ionophores in polyurethane membranes," Analytica Chimica Acta, (2001), pp. 67-78, vol. 432.

Malon, A. et al., "Improving the Detection Limit of Anion-Selective Electrodes: An Iodide-Selective Membrane with a Nanomolar Detection Limit," Anal. Chem. (2003) pp. 3865-3871, vol. 75.

Park, S.B. et al., "Potentiometric Anion Selectivities of Polymer Membranes Doped with Indium(III)-Porphyrins," Electroanalysis (1991) pp. 909-916, vol. 3.

Phadke, A.S. et al., "Synthesis of Carboranyl Porphyrins: Potential Drugs for Boron Neutron Capture Therapy," Tetrahedron Letters, (1993), pp. 1725-1728, vol. 34, No. 11.

Qin, Y. et al., "Plasticizer-Free Polymer Containing a Covalently Immobilized Ca2+-Selective Ionophore for Potentiometric and Optical Sensors," Anal. Chem., (2003), pp. 3038-3045, vol. 75, 13.

Qin, Y. et al., "Plasticizer-Free Polymer Membrane Ion-Selective Electrodes Containing a Methacrylic Copolymer Matrix," Electroanalysis, (2002), pp. 1375-1381, vol. 14, No. 19-20.

Retter, R. et al., "Flow Cytometric Ion Detection with Plasticized Poly(Vinyl Chloride) Microspheres Containing Selective Ionophores," Anal. Chem., (2002), pp. 5420-5425, vol. 74.

Schaller, U. et al., "Ionic Additives for Ion-Selective Electrodes Based on Electrically Charged Carriers," Anal. Chem., (1994) pp. 391-398, vol. 66.

Steinle, E.D. et al., "Origin of Non-Nernstian Anion Response Slopes of Metalloporphyrin-Based Liquid/Polymer Membrane Electrodes," Anal. Chem., (2000), pp. 5766-5773, vol. 72.

Steinle, E.D. et al., "Response Characteristics of Anion-Selective Polymer Membrane Electrodes Based on Gallium (III), Indium(III) and Thallium(III) Porphyrins," Analytical Sciences, (1998), pp. 79-84, vol. 14.

Telting-Diaz, M. et al., "Mass-Produced Ionophore-Based Fluorescent Microspheres for Trace Level Determination of Lead Ions," Anal. Chem. (2002), pp. 5251-5256, vol. 74.

Tsagkatakis, I. et al., "Monodisperse Plasticized Poly(vinyl chloride) Fluorescent Microspheres for Selective Ionophore-Based Sensing and Extraction," Anal. Chem., (2001), pp. 6083-6087, vol. 73.

Xu, Chao et al., "Microsphere optical ion sensors based on doped silica gel templates," Analytica Chimica Acta, (2005), pp. 135-143, vol. 537.

Yoon, I.J. et al., "Potentiometric behavior of metalloporphyrin-based ion-selective electrodes: Use of silicone rubber matrix for serum chloride analysis," Analytica Chimica Acta, (1998), pp. 175-181, vol. 367.

Zhang, W. et al., "Optical Chloride Sensor Based on Dimer-Monomer Equilibrium of Indium(III) Octaethylporphyrin in Polymeric Film," Anal. Chem., (2002), pp. 4548-4557, vol. 74.

Amemiya, S., et al., "A Generalized Model for Apparently 'Non-Nernstian" Equilibrium Responses of Ionophore-Based Ion-Selective Electrodes. 1. Independent Complexation of the Ionophore with Primary and Secondary Ions, Anal. Chem., (2003), pp. 3329-3339, vol. 75.

Ammann, D. et al., "Anion Selectivity of Metalloporphyrins in Membranes," Helvetica Chimica Acta, (1986), pp. 849-854, vol. 69.

Bakker, E., et al., "Anion-Selective Membrane Electrodes Based On Metalloporphyrins: The Influence Of Lipophilic Anionic And Cationic Sites On Potentiometric Selectivity," Talanta, (1994), pp. 881-890, vol. 41, No. 6.

Bakker, E., et al., "Selectivity of Potentiometric Ion Sensors," Anal. Chem., (2000), pp. 1127-1133, vol. 72.

Brasuel, M. et al., "Fluorescent Nanosensors for Intracellular Chemical Analysis: Decyl Methacrylate Liquid Polymer Matrix and Ion-Exchange-Based Potassium Pebble Sensors with Real-Time Application to Viable Rat C6 Glioma Cells," Anal. Chem. (2001) pp. 2221-2228, vol. 73.

Buhlmann, P. et al., "Carrier-Based Ion-Selective Electrodes and Bulk Optodes. 2. Ionophores for Potentiometric and Optical Sensors," Chem. Rev., (1996) pp. 1593-1687; vol. 98.

Byrne, C.J. et al., "A Facile Porphyrin Esterification/Etherification Procedure," Tetrahedron Letters, (1988), pp. 1421-1424, vol. 29, No. 12.

Chaniotakis, N. A. et al., "Influence of Porphyrin Structure on Anion Selectivities of Manganese(III) Porphyrin Based Membrane Electrodes," Anal. Chem. (1988) pp. 185-188, vol. 60.

Chaniotakis, N. A. et al., "Salicylate-Selective Membrane Electrode Based on Tin(IV) Tetraphenylporphyrin," Anal. Chem., (1989), pp. 566-570, vol. 61.

Coutant, D.E. et al., "Selective separation of fullerenes on hydroxyphenyl-triphenylporphyrin-silica stationary phases," Journal of Chromatography A., (1998), pp. 147-157, vol. 824.

Eaton, S.S. et al., "Rotation of Phenyl Rings in Metal Complexes of Substituted Tetraphenylporphyrins," Journal of the American Chemical Society, (1975), pp. 3660-3666, vol. 97, No. 13.

Gao, D. et al., "Nitrite-sensitive Liquid Membrane Electrodes Based on Metalloporphyrin Derivatives," Analyst, (1995), pp. 499-502, vol. 120.

Gorski, L., et al., "Recognition of Anions Using Metalloporphyrin-Based Ion-Selective Membranes: State-of-the-Art," Electroanalysis, (2003) pp. 1229-1235, vol. 15, No. 15-16.

Heng, L.Y. et al., "One-Step Synthesis of K+-Selective Methacrylic-Acrylic Copolymers Containing Grafted Ionophore and Requiring No Plasticizer," Electroanalysis (2000), pp. 178-186, vol. 12, No. 3.

Heng, L.Y. et al., "Producing 'Self-Plasticizing' Ion-Selective Membranes," Analytical Chemistry, (2000), pp. 42-51, vol. 72.

Hodinar, A. et al., "Thiocyanate Solvent Polymeric Membrane Ion-selective Electrode Based on Cobalt(III) Alpha, Beta, Gamma Delta-Tetraphenylporphyrin Anion Carrier," Chemistry Letters, (1988), pp. 993-996.

Huser, M. et al., "Transport Properties of Anion-Selective Membranes Based on Cobyrinates and Metalloporphyrin Complexes as Ionophores," Helvetica Chimica Acta, (1990), pp. 1481-1496, vol. 73.

Jyo, A. et al., "Effect of Membrane Matrices on Performances of a Thiocyanate Ion-Selective Electrode Based on the (5,10,15,20-Tetrapheyl-porphyrinato)manganese(III) Anion Carrier," Analytical Sciences, (1992), pp. 823-827, vol. 8.

Kamachi, M. et al., "Preparation of Polymer Containing Porphyrin Moiety. Radical Polymerization of 5-(4-Acryloyloxyphenyl)-10,15,20-Triphenylporphyrin," J. Polymer Sci.: Polymer Letters Ed., (1983), pp. 693-698, vol. 21.

Shannon E. Stitzel et al., "Array-to-Array Transfer of an Artificial Nose Classifier", The Max Tishler Laboratory of Organic Chemistry, Department of Chemistry, Tufts University, Medford Massachusetts 02155 and Department of Mathematical Sciences, Johns Hopkins University, Baltimore, Maryland 21218, Nov. 1, 2001, pp. 5266-5271 Analytical Chemistry, vol. 73, No. 21.

Robert Retter, "Flow Cytometric Ion Detection With Plasticized Poly (Vinyl Chloride) Microspheres Containing Seletive Ionophores", Department of Chemistry, Auburn University, Auburn, Alabama 36849, and Beckman Coulter, Inc., 200 South Kraemer Blvd., Brea, California 92822, Oct. 15, 2002, pp. 5420-5424, Analytical Chemistry, vol. 74, No. 20.

\* cited by examiner

1
In(OEP)Cl

2
In(HEPEAC)Cl

3
In(AOTPP)Cl

LONG LIVED ANION-SELECTIVE SENSORS BASED ON A COVALENTLY ATTACHED METALLOPORPHYRIN AS ANION RECEPTOR

CROSS REFERENCE TO RELATED APPLICATION

The present application claims the benefit of priority to U.S. Provisional Patent Application No. 60/690,247, filed on Jun. 14, 2005, the entire contents of which are hereby incorporated herein by reference.

STATEMENT REGARDING FEDERALLY SPONSORED RESEARCH OR DEVELOPMENT

This invention was made with the United States Government support under DE14950 awarded by the National Institutes of Health. The United States Government has certain fights in the invention.

BACKGROUND

Metalloporphyrins have been used as ionophores in anion-selective electrodes for many years. They yield selectivity patterns that deviate from the Hofmeister sequence because of the selective axial ligation of the metal. Different metal ions and different porphyrin structures show selectivity for different anions. For example, the use of In $(III)_{(25)}$, $Mn(III)_{(2, 8, 18)}$, $Sn(IV)_{(9, 20)}$, $Ru(II)_{(17)}$, and $Co(III)_{(2, 16, 17, 21)}$ porphyrins has led to the design of a variety of anion sensors with analytically useful selectivities for chloride, thiocyanate, salicylate, thiocyanate, and nitrite/thiocyanate, respectively. However, several of the metalloporphyrin-based anion-selective electrodes exhibit much larger response slopes than the theoretical Nernstian slope.

This "super-Nernstian" behavior has been reported to originate from the dimerization of the electrode response. Therefore, metalloporphyrin-based membranes must normally be metalloporphyrins via hydroxide ion bridges. Briefly, the membranes are considered to respond to two ions, for example chloride and hydroxide, simultaneously, which, theoretically, results in a pH codependence of measured in pH-buffered samples.

The electrode slopes for the metalloporphyrin-based membranes often change with different amounts of ion exchanger used in the membranes. $_{(3, 25, 32)}$ The super-Nernstian response slope has been explained on the basis of the extremely small, and drastically changing, concentration of uncomplexed ionophore in the membrane. As the concentration of sample anion is increased, for example, hydroxide ions are expelled from the membrane on the basis of the ion-exchange equilibrium. This process starts breaking down the porphyrin dimers, which are held together by hydroxide bridges. $_{(31)}$ Consequently, the concentration of uncomplexed ionophore in the membrane starts increasing, which leads to a decrease in the uncomplexed chloride concentration in the membrane. This membrane concentration decrease upon increasing the sample concentration leads to the apparently super-Nernstian response slope.

Others have argued that the super-Nemstian slope described above indicates a higher sensor sensitivity and may therefore be beneficial. However, it was reported that the response time of such membrane electrodes is prohibitively slow. $_{(30)}$ Moreover, the response model demands that the membrane should be cross-responsive to another ion as well, in this case to OH$^-$ (or H$^+$). To our knowledge, no experimental evidence has yet been presented in the literature that would support this second point, at least for the In$^{III}$octaethylporphyrin studied here (see FIG. 1 for structure).

The properties and applications of the well-established chloride ionophore, indium$^{III}$octaethylporphyrin (In(OEP)Cl), in ion-selective electrodes and optodes have been studied extensively. This ionophore may easily form dimers via hydroxide ion bridges in polymeric membranes. The monomer-dimer equilibrium has been used for the preparation of a chloride-sensing optode. Still, the dimerization of metalloporphyrins leads to several disadvantages in ion sensors.

While ISE membranes based on metalloporphyrins should suffer from a pH cross response, the formation of indium porphyrin dimers also leads to a much reduced sensor lifetime. $_{(36)}$ The dimeric species is not very soluble in plasticized PVC membranes and crystallization easily occurs once the membranes or films contact an aqueous solution.

Alternative matrixes for solid-state sensors such as polyurethane $_{(23)}$ and silicon rubber $_{(35)}$ have been studied for preparing metalloporphyrin-based ion-selective membranes. Unfortunately, similar to plasticized PVC membrane, the sensors also showed super-Nernstian responses and a short lifetime. Only the In(OEP)Cl-based polyurethane membrane was reported to exhibit a Nernstian slope to chloride ion but not to other more selective anions. The formation of the dimers in these membrane matrixes was confirmed by the appearance of the Soret band at 390 nm for the dimeric species when the membranes were soaked in aqueous solution. $_{(23)}$ The covalent attachment of ionophores to a methacrylate copolymer has been studied by a number of research groups $_{(4, 15, 22)}$ and by our own laboratory $_{(27)}$. Recently, a methyl methacrylate and decyl methacrylate copolymer was developed for preparing plasticizer-free ion sensors $_{(28)}$ in order to overcome the disadvantages of plasticized PVC membranes, including the leaching of plasticizer in miniaturized sensing configurations. $_{(5, 9, 33, 34)}$

SUMMARY

It has been discovered that covalent attachment of metalloporphyrin ionophores to a copolymer eliminates two principal reasons responsible for the unsatisfactory performance of metalloporphyrins in ion-selective sensors, namely poor solubility and non-Nemstian response slopes. Formation of a graft copolymer containing covalently attached ionophores eliminates the formation of undesired metalloporphyrin dimers. Moreover, use of the graft copolymer in the context of anion-selective sensors advantageously shortens response and recovery times and increases sensor lifetime.

Accordingly, the present invention is directed to a graft copolymer having selectivity for a target anion, which is comprised polymerized units of (a) a functionalized ionophore monomer comprising a metalloporphyrin and a polymerizable group; and (b) a co-monomer, wherein at least a portion of the functionalized ionophore is covalently attached to the copolymer in a manner preventing formation of metalloporphyrin dimers.

In another aspect, the present invention is directed to a method of making a graft copolymer having selectivity for a target anion, by polymerizing the functional ionophore monomer and the co-monomer to form a copolymer, wherein at least a portion of the functionalized ionophore is covalently attached to the copolymer in a manner preventing formation of metalloporphyrin dimers.

In yet another aspect of the present invention is directed to the functionalized ionophore monomer, as well as a method of making a functionalized ionophore monomer, which includes attaching a spacer moiety to a porphyrin base to form a porphyrin derivative, forming a metal complex with the porphyrin derivative to form a metalloporphyrin derivative; and modifying the metalloporphyrin derivative by introducing a polymerizable group to the spacer.

Further, the graft copolymer can be blended with another polymer, such as poly(vinyl chloride) or polyurethane, and a plasticizer to provide an anion-selective membrane having improved mechanical properties. These anion-selective membranes can be adapted for use in a variety of anion-detecting sensors, which are capable of detecting a target anion interaction with the ionophore, such as anion-selective electrodes or optodes.

BRIEF DESCRIPTION OF THE DRAWINGS

These features, aspects and advantages of the present invention will become better understood with regard to the following description, appended claims and accompanying drawings where:

DETAILED DESCRIPTION

Figure 1:
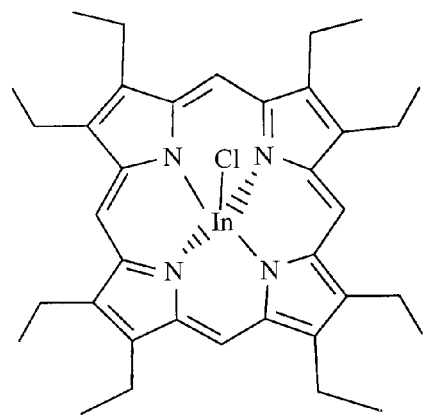
FIG. 1 shows structures of the three iridium$^{III}$ porphyrin ionophores In(OEP)Cl, In (HEPEAC)Cl, and In(AOTPP)Cl.
Figure 1:
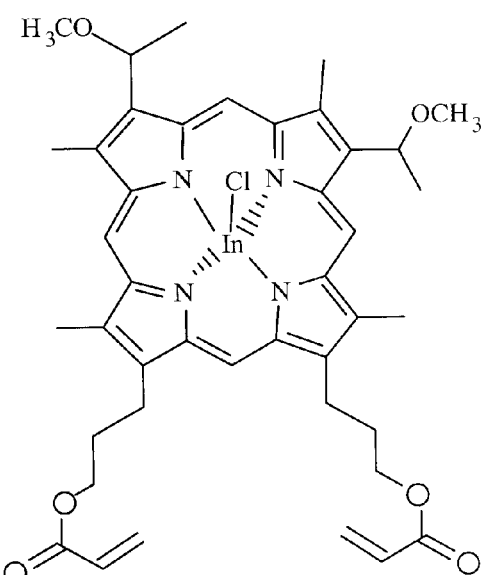
Figure 1:
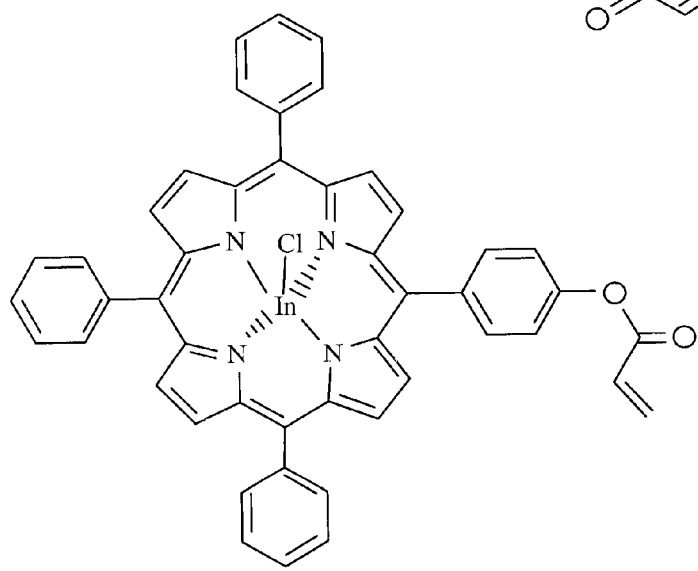

The present invention overcomes problems associated with spontaneous hydroxy-bridged dimer formation of metalloporphyrins in ion-selective membranes. Dimerization gives rise to a short sensor lifetime (typically days), triggered by solubility problems, the occurrence of a super-Nernstian response slope, and a pH cross response. This dimer formation is eliminated here by covalent attachment of the ionophore to the polymer matrix. Moreover, covalent attachment of the metalloporphyrin ionophore advantageously shortens response and recovery times of anion-selective sensors to a matter of seconds rather than minutes.

The invention relates to a graft copolymer having selectivity for a target anion comprising polymerized units of a functionalized metalloporphyrin monomer and a co-monomer, wherein at least a portion of the functionalized ionophore is covalently attached to a copolymer in a manner preventing formation of metalloporphyrin dimers.

The terms "functionalized metalloporphyrin monomer" or "functionalized ionophore" refers to a metalloporphyrin ionophore having a reactive functional group, which allows the ionophore to become covalently bonded to a copolymer. The functional group is required to allow the ionophore to react with a reactive group of the copolymer, such as a carbon-carbon double bond, to form covalent linkages, whereby the ionophore becomes covalently grafted onto the copolymer. Examples of such functional groups include, but are not limited to, carbon-carbon double bonds, such as acrylic and methacrylic groups, carbon-carbon triple bonds and carbonyl groups.

The terms "covalently grafted ionophore," "covalently anchored ionophore," and "covalently immobilized ionophore" are used interchangeably herein and refer to an ionophore that is attached to a polymer through covalent bonds.

Metalloporphyrins suitable for use as ionophores in the graft copolymer can incorporate different metal ions and different porphyrin structures, which show selectivity for different anions. For example, the use of In (III), Mn(III), Sn(IV), Ru(II), and Co(III) porphyrins has led to the design of a variety of anion sensors with analytically useful selectivities for chloride, thiocyanate, salicylate, thiocyanate, and nitrite/thiocyanate, respectively.

Examples of anion selective ionophores suitable for purposes of this invention include porphyrins, such as hematoporphyrins, octaethylporphyrins, tetraphenylporphyrins and derivatives thereof. Metalloporphyrins of the type described herein are well known in the art and are commercially available or may be prepared using conventional methods known in the art.

Functionalized metalloporphyrin monomers in accordance with the invention can be synthesized, for example, by methods described in Example 1. The method of making the functionalized ionophore monomer will typically include: (1) providing a porphyrin base; (2) attaching a spacer moiety to the porphyrin base to form a porphyrin derivative; (3) forming a metal complex with the porphyrin derivative to form a metalloporphyrin derivative; and (4) modifying the metalloporphyrin derivative by introducing a polymerizable group to the spacer.

Specifically, two different indium$^{III}$porphyrins containing polymerizable groups, the chloride-selective chloro(3-[18-(3-acryloyloxypropyl)-7,12-bis(1-methoxyethyl)-3,8,13,17-tetramethylporphy-rin-2-yl]propyl ester)indium (III) and the nitrite-selective Chloro (5-(4-acryloyloxyphenyl)-10,15,20-triphenylporphyrinato)indium(III), were synthesized and copolymerized with methyl methacrylate and decyl methacrylate. The covalent attachment of the ionophore to the polymer matrix indeed prevents the metalloporphyrin from forming dimeric species, as confirmed by UV/visible spectroscopy.

The terms' "polymer" and "copolymer" are used interchangeably and refer to a chemical compound or mixture of compounds formed by polymerization and comprising repeating monomer units, wherein the polymer can comprise one type of monomer unit or can contain two or more different monomer units.

Preferred polymers will have adequate solubility in organic solvents so that they can be mixed with the other components and can be converted into coatings by conventional coating methods. They should furthermore be permeable to ions. The dielectric constant of the polymers is preferably from 2 to 25, particularly preferably from 5 to 15, at 100 Hz and room temperature. The optical transparency is preferably in the range from 400 to 1200 nm, particularly preferably from 400 to 900 nm.

Suitable polymers are known to the person skilled in the art. They can be homopolymers, copolymers, block polymers, graft polymers and polymer alloys. The components of a polymer alloy may be a combination of two or more polymer components, said components having high and low glass transition temperatures. The glass transition temperature can be adjusted, for example, by means of the polarity and the chain length and content of structural units. The glass transition temperature is preferably from −130 to 0° C. Polymers with very low $T_g$ values are normally much softer and more difficult to handle mechanically. The $T_g$ is typically determined experimentally with a differential scanning calorimeter, a standard instrument for this purpose.

The polymers can be selected, for example, from the group consisting of polyolefins, polyesters, polyamides, polyethers, polyimides, polyesteramides, polyamideimides, polyurethanes, polyetherurethanes, polyesterurethanes, polyureas, polyurethaneureas and polysiloxanes, it being possible for the polymers to contain ionizable, basic groups (for example amino groups) or ionizable, acidic groups (for example carboxyl or sulfonyl groups), which may be used as replacement for a counterion of lipophilic salts and can provide improved ion transport Some examples of monomers for the preparation of polyolefins are $C_2$-$C_{12}$ olefins, acrylic acid, methacrylic acid, maleic acid, maleic anhydride, $C_1$-$C_{30}$ esters of acrylic and methacrylic acid, $C_1$-$C_{30}$ amides of acrylic and methacrylic acid, acrylamide and methacrylamide, vinyl esters of $C_1$-$C_{20}$ carboxylic acids, acrylonitrile, butadiene, isoprene, chlorobutadiene, styrene, α-ethylstyrene, vinyl chloride, vinyl fluoride, vinylidene chloride and vinyl ethers of $C_1$-$C_{30}$ alcohols.

Polyesters, polyesteramides and polyamides are preferably synthesized from $C_2$-$C_{12}$ dicarboxylic acids and $C_2$-$C_{18}$ diols or -diamines. Polyimides are preferably synthesized from $C_2$-$C_{18}$ tetracarboxylic acids and $C_2$-$C_{18}$ diamines. Polyethers are preferably synthesized from aliphatic $C_2$-$C_{12}$ diols (1,2- or α, ω-lining) or linear adducts of these diols and $C_8$-$C_{30}$ diglycidyl ethers. Polyurethanes and polyureas are preferably synthesized from $C_2$-$C_{18}$ diols or -diamines and $C_2$-$C_{20}$ diisocyanates and/or triisocyanates. Polysiloxanes are preferably synthesized from di($C_1$-$C_4$)alkylsilyldichlorosilanes In a preferred embodiment, the polymers comprise a copolymer of methacrylate monomers with different pendant alkyl groups $R_1$ and $R_2$, wherein $R_1$ may be any of $C_{1-3}$ alkyl group, and $R_2$ may be any of $C_{4-12}$ alkyl group.

As used herein, the term "alkyl" refers to a saturated linear or branched-chain monovalent hydrocarbon radical of one to twelve carbon atoms, wherein the alkyl radical may be optionally substituted independently with one or more substituents described below. Examples of alkyl groups include, but are not limited to, methyl, ethyl, n-propyl, isopropyl, butyl, isobutyl, sec-butyl, tert-butyl, pentyl, isopentyl, tert-pentyl, hexyl, isohexyl, and the like In accordance with embodiments of the present invention, preferably $R_1$ is a $C_{1-2}$ alkyl group, and $R_2$ is a $C_{8-12}$ alkyl group. In one embodiment, methyl methacrylate and decyl methacrylate monomers are used for forming a methyl methacrylate-decyl methacrylate (MMA-DMA) copolymer matrix of the present invention.

Methacrylate monomers of the present invention are commercially available from, for example, Polysciences, Inc. (Warrington, Pa.). Alternatively, the methacrylate monomers can be prepared by standard methods known in the art or via thermally initiated free radical solution.

In one embodiment, the metalloporphyrin ionophore comprises a polymerizable group, and the ionophore is covalently grafted onto a polymer chain by copolymerizing the ionophore monomer with methacrylate co-monomers such as MMA and DMA monomers. In this embodiment, the copolymer may comprise a random distribution of immobilized ionophore within the MMA-DMA polymer chain.

Graft copolymers of the present invention comprising a covalently grafted ionophore may be made in accordance with methods known in the art or the methods described herein. For example, in one embodiment the graft copolymer is prepared by thermally initiated free radical solution polymerization of a mixture of methacrylate monomers and a functionalized ionophore as described herein in detail in Example 2.

Alternatively, other methods known in the art may be used to covalently graft the ionophore to the matrix. For example, a sol-gel technique may be used to prepare the graft copolymer. Another approach involves directly grafting the ionophore onto an existing polymer with active sites. Yet another approach involves blending two different polymers together, with one of them containing the grafted ionophore. Alternatively, a solution containing methacrylated monomers and the functionalized ionophore can be irradiated with an electron beam to cause polymerization and covalent attachment of the functionalized ionophore onto the methacrylate copolymer.

A sufficient amount of functionalized ionophore is combined with the copolymer to obtain the desired improvement in desired properties of the copolymer, such as reduced dimer formation, anion selectivity, faster response and recovery times and extended lifetime. Such properties may be quantitatively measured by well-known test methods. For example, spectophotometric measurements can be used to assess porphyrin dimer formation as described in Examples 3 and 8.

The optimal amount of functionalized ionophore required to produce a significant enhancement of such properties will, of course, vary depending upon the chemical compositions, structures, and molecular weights of the components employed as well as the extent of grafting achieved. The graft copolymer typically contains the ionophore in, for example, an amount of from 0.01 to 10% by weight, preferably from 0.1 to 5% by weight, based on the amount of polymer. In general, however, it will be advantageous to use at least one part by weight of the functionalized ionophore for every 100 parts by weight of the copolymer. When the functionalized ionophore is an indium porphyrin, the ionophore is added in an amount between about 1-5% by weight, with 5% being preferred.

The conditions necessary to achieve at least partial grafting of the components of the polymer composition will vary depending upon the reactivities of the individual components. For example, when the ionophore comprises an acrylic functional group [as with In(AOTPP)Cl or In(HEPEAC)Cl] which can react with the methacrylate monomer unit of the copolymer, then the grafting conditions may comprise a thermal or photoinitiated co-polymerization in an organic solvent such as benzene. When indium porphyrins were grafted onto a MMA-DMA copolymer, the amount of indium porphyrin monomers that polymerized with the MMA and DMA monomers was measured to be about 70%.

The graft copolymer will expediently have a mean molecular weight of at least 5 000, preferably at least 10 000 and particularly preferably at least 20 000 daltons, for example from 20 000 to 200 000 daltons, preferably from 50 000 to 200 000 daltons.

In one embodiment, the graft copolymers of this invention may be blended, admixed, or combined with other polymers to obtain blends having improved properties or performance characteristics.

For example, the polymer composition when blended with poly(vinyl chloride) or polyurethane and a plasticizer, such as DOS or NPOE, has the beneficial effect of increased mechanical robustness. The relative proportion of PVC polymer:graft polymer composition may be varied as desired, preferably from about 90:10 to 80:20 on a weight basis.

The ion-detecting polymer of the present invention may also include other additives such as an ion-exchanger, most preferably sodium tetrakis[3,5-bis(trifluoromethyl)phenyl]borate, to enhance the extraction of the target ion from the aqueous sample and the migration of the target ion into the polymer matrix.

The graft polymers and blended polymer compositions of the present invention can be adapted for use in a variety of anion-selective sensors capable of detecting the interaction of a target anion with the ionophore. For example, the graft polymers and blended polymer compositions may be used to fabricate ion-selective membranes, films or particles, which include, but are not limited to, carrier-based ion-selective electrodes (ISEs), thin film ion-specific optodes, particle-based optodes, and bulk optodes.

For example, a graft polymer of this invention may be used to fabricate polymer membranes of an ion-selective electrode (ISE) in accordance with methods described in Examples 3 and 7 of the present invention or any other methods known to one skilled in the art.

The ion-selective membranes with grafted indium porphyrin showed Nernstian response slopes to chloride, nitrite, perchlorate, and thiocyanate anions, with a selectivity comparable to membranes with freely dissolved or underivatized metalloporphyrin. The membranes containing grafted ionophores showed a lifetime of at least two months, apparently since crystallization of the poorly soluble dimeric species may no longer occur. Moreover the response and recovery times of the membranes were greatly reduced to a matter of seconds, rather than minutes. This is one of the first examples where the covalent attachment of an ionophore drastically improves on a number of important sensor characteristics.

Polymers of this invention may also be used to fabricate thin films to be used in a thin film ion-specific optode or to fabricate microsphere particles to be used in particle-based optodes in accordance with methods known in the art. For example, the electrodes and optodes may be prepared, for example, by solvent casting and spin coating techniques.

Optodes may also include an indicator dye to provide a detectable signal suitable for the optical determination of ions in an aqueous environment, in particular by measurement of the change in fluorescence. Examples of indicator dyes include, but are not limited to, a pH indicating chromoionophore, a chromoionophore, a fluoroionophore, a pH indicator, or a pH indicating fluoroionophore.

The indicator dyes to be used according to the invention will have suitable absorption and emission wavelength ranges which allow the use of known and inexpensive light sources, for example halogen or xenon lamps or light-emitting diodes. Examples of detectors which can be employed are photodiodes. In addition to fluorescence spectroscopy, other optical measurement methods may also be used, for example surface plasmoresonance spectroscopy, absorption spectroscopy, reflection spectroscopy, interferometry or surface-amplified Raman or fluorescence spectroscopy.

The ion-detecting sensors of the present invention may be used for detecting ions of all types of body fluid samples. Examples of the samples include, but are not limited to, whole blood, spinal fluid, blood serum, urine, saliva, semen, tears, etc. The fluid sample can be assayed neat or after dilution or treatment with a buffer.

EXAMPLE 1

Synthesis of Polymerizable Metalloporphyrin Monomers

Reagents. Hematoporphyrin base was obtained from Frontier Scientific (Logan, Utah); octaethylporphyrin, indium (III) chloride, orthoformate, methanol, sulfuric acid, 4-hydroxybenzaldehyde, benzaldehyde, pyrrole, propionic acid, acetic acid, acryloyl chloride, triethylamine and 1-octanol were purchased from Aldrich (Milwaukee, Wis.). All anhydrous solvents used for syntheses were obtained from Fisher Scientific (Pittsburgh, Pa.). The monomers methyl methacrylate, 99.5%, and n-decyl methacrylate, 99%, were obtained from Polysciences, Inc. (Warrington, Pa.). The polymerization initiator 2,2'-azobisisobutyronitrile, 98% (AIBN), was obtained from Aldrich. Inhibitors were removed from the monomers by distillation. AIBN was recrystallized from warm methanol prior to use. Sodium tetrakis[3,5-bis(trifluoromethyi)phenyl]borate (NaTFPB), o-nitrophenyl octyl ether (NPOE), bis(2-ethylhexyl) sebacate (DOS), high molecular weight polyvinyl chloride) (PVC), polyurethane, tetrahydrofuran (THF), and all salts were purchased in Selectophore or puriss quality from Fluka (Milwaukee, Wis.). Aqueous solutions were prepared by dissolving the appropriate chloride salts in Nanopure purified water (18 MQ cm).

Syntheses of Porphyrins. Hematoporphyrin dimethyl ester dimethyl ether was synthesized from hematoporphyrin IX base by esterification and etherification.$_{(7)}$ Hematoporphyrin dimethyl ester dimethyl ether was then reduced by $LiAlH_4$ to give 21H, 23H-porphine-2,18-dipropanol 7,12-bis(1-methoxyethyl)-3,8,13,17-tetramethyl-(9Cl) (HEPE) as reported. $_{(26)}$ 5-4(-Hydroxyphenyl)-10-15-20-triphenylporphyrin (TPP) was prepared as reported.$_{(10,19)}$ Syntheses of Indium Complexes. In(OEP)Cl (1, MW 684.4) was synthesized as reported. Polymerizable indium complexes chloro(3-[18-(3-acryloyloxypropyl)-7,12-bis(1-methoxyethyl)-3,8,13,17-tetramethylporphyrin-2-yl]-propyl ester) indium (III) (In(HEPEAC)-Cl, 2, MW 855.14) and chloro(5-(4-acryloyloxyphenyl)-10,15,20-triphenylporphyrinato) indium (III) (In(AOTPP)Cl, 3, MW 833.03) were prepared by the following two steps. Step one: the procedure used to synthesize the indium complexes In (HEPE) Cl and In(HOTPP)Cl was analogous to the literature. Step two: indium porphyrins In (HEPE) Cl and In(HOTPP)Cl were dissolved in dry $CH_2Cl_2$ with $N_2$ protection. Subsequently, triethylamine was added to the solution. Afterward, acryloyl chloride was added dropwise to the reaction mixture with a syringe under $N_2$ at $-5°$ C. After 25 min, 30 mL of a saturated $N_aHCO_3$ solution was added to quench the reaction. The organic phase was then separated and washed with water. After evaporation of the solvent, the crude product was purified by flash chromatography. Final products were characterized by $^1$NMR.In(AOTPP)Cl: $\delta_H$ (250 MHz; $CDCl_3$) 9.01 (m, 8H); 8.41 (m, 4H); 8.17 (m, 4H); 7.84 (m, 9H); 7.61 (m, 2H); 6.85 (m, 1H); 6.57 (m, 1H); 6.19 (m, 1H). In(HEPEAC)Cl: $\delta_H$ (400 MHz; $CDCl_3$) 10.56 (s, 1H); 10.51 (s, 1H); 10.11 (s, 1H); 9.98 (s, 1H); 6.49 (m, 2H); 6.29-6.20 (m, 2H); 6.05 (q, 2H); 5.87 (m, 2H); 4.48 (m, 4H); 4.15 (m, 4H); 3.71 (s, 6H); 3.62 (s, 6H); 3.61 (s, 6H); 2.67 (m, 4H); 2.27 (m, 6H).

EXAMPLE 2

Polymer Synthesis and Characterizations. All polymers were synthesized via thermally initiated free radical solution polymerization. The amount of methyl methacrylate (MMA) and n-decyl methacrylate (DMA) used was the same as reported previously.$_{(27,28)}$ For polymers containing grafted ionophores, 5 wt % indium porphyrins (50 mg), 0.78 g of MMA, and 0.20 g of DMA were dissolved in anhydrous EtOAc. The solution was purged with $N_2$ for 10 min before adding 5.1 mg of AIBN. The homogeneous solution was continuously stirred, and the temperature was ramped to 90° C., which was maintained for 16 h. After the reaction was complete, the solvent was evaporated and the polymer was redissolved in 10 mL of dioxane. Aliquots of polymer solution (2 mL) were added to 100 mL of distilled water under vigorous stirring. The precipitate was collected and dissolved in 25 mL of dichloromethane, followed by water removal with anhydrous $Na_2SO_4$ and filtering. The solvent was evaporated, and the resultant polymer was washed with methanol to ensure the complete removal of the free ionophores. The polymer was dried under ambient laboratory conditions. The copolymers with grafted ionophores were characterized by $^1$HNMR to confirm the covalent attachment. According to the reported method, the concentration of the grafted indium porphyrins in the polymer was estimated by $^1$HNMR as 45 mmol/kg (70% yield). The molecular weight of the copolymer was measured by PLGel Mixded-C columns (Polymer Laboratories Inc., Amherst, Mass.) with stabilized THF as the carrier solvent and polystyrene as standard.

EXAMPLE 3

ISE Membrane Preparation and Measurements. ISE membranes containing free ionophores were prepared by dissolving NaTFPB (optionally, 3 mmol/kg), ionophore (10 mmol/kg, if used), PVC or polyurethane, and plasticizer (DOS or NPOE) in a 1:2 ratio by mass to give a total cocktail mass of 140 mg in 1.5 mL of THF. For the membrane with grafted ionophore, the cocktail contained 20 wt % copolymer (~10 mmol/kg ionophore), 3 mmol/kg NaTFPB and PVC, and plasticizer (1:2 mass ratio) in THF. Cocktails were poured into glass rings (2.2 cm i.d.) affixed onto glass microscope slides. The solvent was evaporated overnight to give a transparent membrane. The parent membranes were then conditioned overnight in 0.01 M NaCl. Disks 6 mm in diameter were cut from the parent membranes and mounted into Philips electrode bodies (IS-561, Glasblaserei Möller, Zurich, Switzerland). A 0.01 M solution of NaCl was used as the inner filling solution. For pH titrations, buffer solutions were 10 mM citric acid and 10 mM boric acid with the indicated concentrations of NaCl (either 10 or 0.1 mM) adjusted to pH 1.5 by 1 M standard HCl or 10 mM phosphate buffer solution with NaCl as background. The solution was titrated with a 0.1 M standard NaOH solution, and a pH electrode was used to monitor the sample pH. All experimental results given are the average of at least three electrodes, with calculated standard deviations. Electrode slopes were obtained in the concentration range of of $10^{-5}$-$10^{-2}$ M.

Optical Measurements. The composition of the cocktail was the same as for ion selective membranes. A 50-µL sample of the cocktail was dropped onto the surface of quartz slides. The solvent was allowed to evaporate for 1 h. The absorbance spectra of dry films and films conditioned in 0.05 M MES buffer at pH 5.5 were recorded with a HP 8452 A diode array spectrophotometer.

EXAMPLE 4

Figure 2:
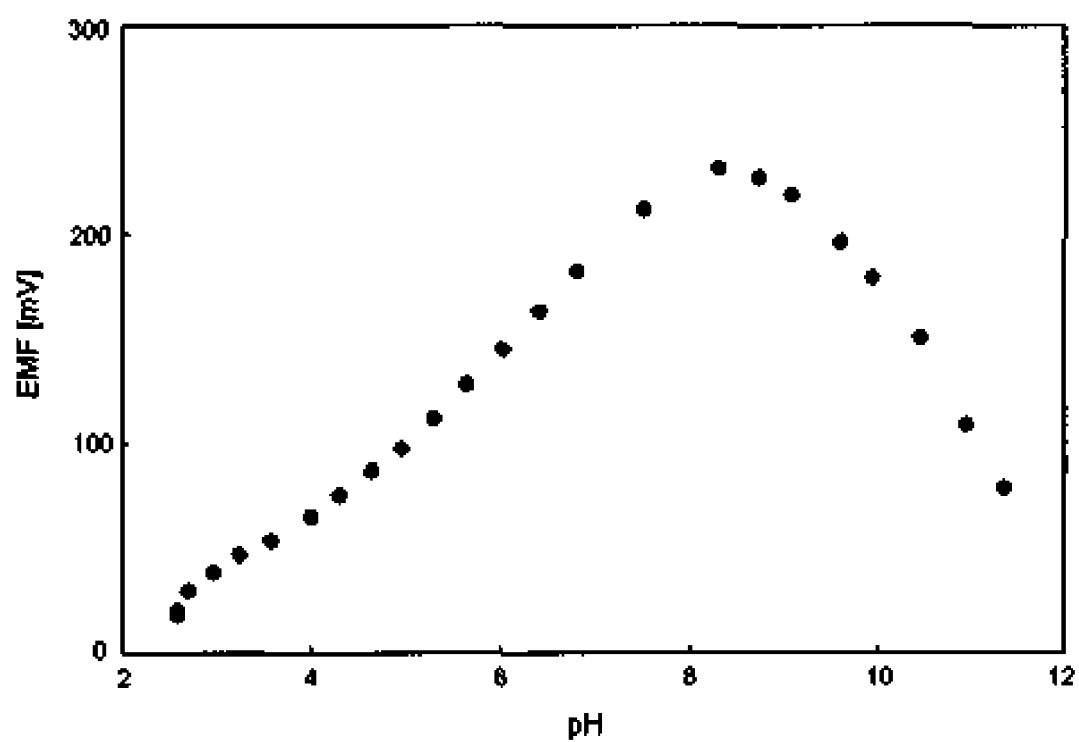
FIG. 2 shows the experimental pH response curve of an In(OEP)Cl-based PVC-NPOE membrane in a 10 mM NaCl background electrolyte.

As shown in FIG. 2, a PVC-NPOE membrane containing this ionophore, in a background of NaCl, indeed suffers from a strong pH dependence in the entire measuring range. For pH values lower than 8.5, the membrane exhibits a response with an inverted positive slope of +45 mV/decade, while in the higher pH range, the slope is closer to Nernstian (−52 mV/decade) for the response to hydroxide.

An inverted slope can be rationalized on the basis of the same response model discussed above. An increase in the sample pH should lead to an increase of the uncomplexed chloride concentration in the membrane (because the ion-exchange process leads to a decreased concentration of uncomplexed ionophore), giving a more positive potential. This result may be also explained by a recent generalized model for apparently "non-Nemstian" response slopes.

The same pH titration experiments were also performed with phosphoric acid rather than citric acid buffer, giving results essentially identical to the data shown in FIG. 2. This confirms that the pH response of the membranes is due to indium porphyrin ionophore chemistry, rather than simple partitioning of citric acid into the membrane at lower pH. The strong pH dependence of the metalloporphyrin-based membrane response, even in the neutral pH range, is a practical drawback because the measurements of such electrodes either require a pH-buffered sample or the simultaneous measurement of pH.

EXAMPLE 5

Another, probably even more important disadvantage of $In^{III}$octaethylporphyrin-based sensors is their short lifetime. While In-(OEP)Cl has been used as a chloride ionophore in ion-selective electrodes and optodes,$_{(36)}$, formation of hydroxide-bridged dimers is observed quickly upon initial contact with aqueous solution. Dimeric species are not very soluble in the polymeric matrix, and the rapid crystallization results in a much reduced lifetime of the sensors. $_{(36)}$ So far, such dimerization and crystallization processes of free indium porphyrin ionophores have been observed in all different types of ISE membranes, and the short lifetime is a common disadvantage of such sensors.

It was contemplated that a covalent attachment of the ionophore to the polymer matrix would lead to a reduction of dimer formation of metalloporphyrins in ion-selective membranes, mainly because of an increased steric hindrance of the porphyrins and decreased flexibility of the polymer chains relative to freely dissolved components. Covalent grafting could likely also reduce or eliminate the undesired crystallization because covalently anchored porphyrins may no longer precipitate.

For this reason, two indium porphyrin complexes with polymerizable groups, In(AOTPP)Cl (3) and In(HEPEAC)Cl (2), were prepared. The covalent attachment of the ionophores was performed by a one-step polymerization with MMA and DMA. The polymers were purified and washed with methanol to remove free ionophores and monomers.

Figure 3:
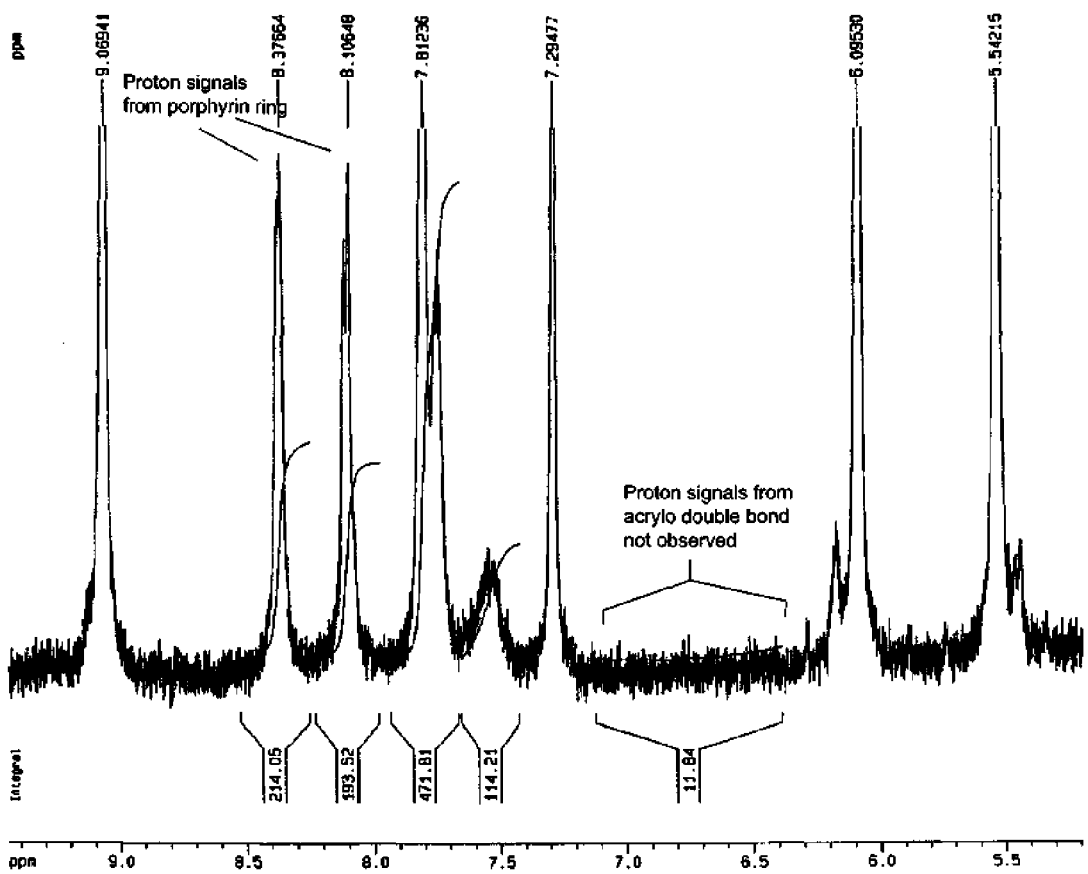
FIG. 3 shows the proton FTNMR spectrum of the copolymer In(AOTPP)Cl-MMA-DMA, indicating complete covalent attachment of the iridium porphyrin monomer.

The molecular weight properties of the copolymers were characterized by gel permeation chromatography. The respective peak, number and weight molecular averages were determined as Mp 59,474, Mn 29,992, and Mw 56,904. The molecular weight distribution (PD) is 1.8, which is similar to the reported values of other blank methacrylate polymers and polymers with grafted ionophores. $_{(14, 15)}$ The NMR spectrum of the In(AOTPP)Cl-MMA-DMA, as shown in FIG. 3, was used to directly confirm the immobilization of the ionophores. The proton signals of the porphyrin ring ($\delta$=7.8-8.6 ppm) and those from the double bond of acrylate group ($\delta$=6.4-7.6 ppm) were used simultaneously. The NMR spectrum of the copolymer indicated proton signals of the aromatic rings but not those related to the double bond of the acryloyl moiety, which suggested the destruction of the double bond and the covalent attachment of the ionophore to the polymer.

EXAMPLE 6

The new polymerizable indium porphyrin ionophores were first characterized classically, without covalent anchoring, in plasticized PVC membranes. Due to the similar structure to In(OEP)Cl, In-(HEPEAC)Cl was characterized as an electrically charged chloride ionophore. $_{(30)}$ According to the charged carrier mechanism $_{(30)}$, a cation exchanger, NaTFPB, was used in the In(HEPEAC)Cl-based membranes to improve the selectivity of the electrodes. Their slopes and selectivities of chloride over nitrate, nitrite, perchlorate, and thiocyanate are given in Table 1.

that the polar plasticizer NPOE is more suitable than nonpolar plasticizer DOS for indium porphyrin-based ion-selective membranes. $_{(1, 25)}$

EXAMPLE 7

Figure 4:
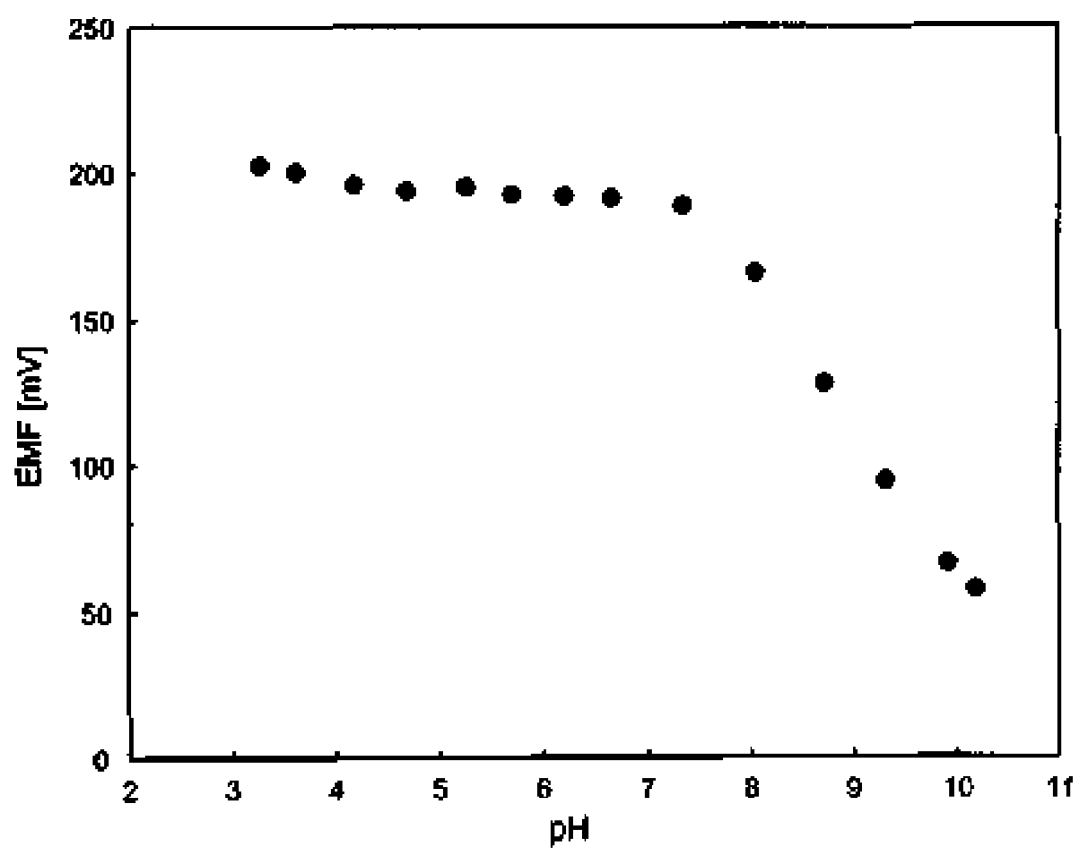
FIG. 4 shows the experimental pH response curve of a PVC-NPOE membrane containing 20% wt % In (HEPEAC) Cl-MMA-DMA and 3 mmol/kg NaTFPB, in a 1 mM NaCl background electrolyte (compare to FIG. 2)

In contrast to the free ionophore-based membranes, we expected that the covalent attachment of indium porphyrin ionophores can prevent the formation of the dimers in polymer membranes. Each MMA-DMA polymer with grafted indium(III) porphyrin was blended with PVC and NPOE to prepare the ion-selective membranes. FIG. 4 shows the pH response of such membrane. Clearly different from the pH

TABLE 1

Electrode Slopes and Logarithmic Selectivity Coefficients' of Plasticized PVC Membranes Containing Free In(HEPEAC)Cl and 30 mol % NaTFPB and Comparison to Corresponding In(OEP)Cl-Based Membranes

| | free In(HEPEAC)Cl PVC-DOS | | free In(HEPEAC)Cl PVC-NPOE | | In(OEP)Cl PVC-NPOE[36] |
|---|---|---|---|---|---|
| ion J | Slope | log $K_{ClJ}^{pnt}$ | Slope | log $K_{ClJ}^{pnt\,a}$ | log $K_{ClJ}^{pnt\,a}$ |
| $NO_3^-$ | −31.1 ± 1.0 | −2.29 ± 0.08 | −52.5 ± 2.0 | −3.08 ± 0.10 | −4.1 |
| $ClO_4^-$ | −45.4 ± 1.2 | −1.06 ± 0.03 | −65.7 ± 1.6 | −1.36 ± 0.08 | −2.0 |
| $NO_2^-$ | −53.2 ± 1.4 | 0.54 ± 0.12 | −93.4 ± 1.5 | 0.31 ± 0.12 | 1.1 |
| $SCN^-$ | −53.8 ± 0.8 | 1.00 ± 0.06 | −95.9 ± 1.3 | 0.88 ± 0.04 | 1.8 |
| $Cl^-$ | −54.8 ± 1.4 | 0 | −92.8 ± 1.3 | 0 | 0 |

$^a$ Selectivity coefficients are not reliable if the indicated electrode slopes are non-Nernstian As with the traditional In(OEP)Cl, PVC-NPOE membranes containing free In(HEPEAC)-Cl showed super-Nernstian responses to chloride and other anions. In PVC-DOS membranes, the ionophores showed near Nernstian response slopes, calculated in the range of $10^{-5}$-$10^{-2}$ M. Such desirable response slopes were also obtained for In(OEP)Cl-based PVC-DOS and polyurethane membranes, which indicated that the dimeric species is less preferred in PVC-DOS membranes than in PVC-NPOE membranes. $_{(23)}$ Unfortunately, crystallization of the ionophore in PVC-DOS is much faster than in PVC-NPOE membranes as the electrodes lost their optimal slopes and selectivities just 2 days after fabrication (data not shown). The result agrees with the accepted notion response of free ionophore-based membranes (FIG. 2), the membrane containing grafted ionophore in 1 mM NaCl showed no pH response from pH 2 to 7.5. Note that the lower NaCl concentration was chosen for this system to avoid any influence of sodium interference on this study (see discussion of upper detection limit below). The hydroxide interference at higher chloride concentrations is predicted to start at proportionally higher pH values. The potentiometric responses of the membranes with and without cation exchanger are compared in Table 2.

TABLE 2

Electrode Response Slopes and Logarithmic Selectivity Coefficients of Free In(HEPEAC)Cl in PVC/IMPOE Membrane Blended with 20 wt % Blank MMA-DMA and the Grafted In(HEPEAC)Cl-Based PVC-NPOE Chloride-Selective Membranes with and without 30 mol % Cation Exchanger NaTFPB

| | free In(HEPEAC)Cl in PVC/NPOE with blank MMA-DMA | | grafted In(HEPEAC)Cl in PVC/NPOE | | | |
|---|---|---|---|---|---|---|
| | (20 wt %) 30 mol % NaTFPB | | no NaTFPB | | 30 mol % NaTFPB | |
| ion J | Slope | log $K_{ClJ}^{pnt\,a}$ | Slope | log $K_{ClJ}^{pnt\,a}$ | slope | log $K_{ClJ}^{pnt}$ |
| $NO_3^-$ | −38.7 ± 1.0 | −3.58 ± 0.02 | −17.2 ± 2.0 | −2.02 ± 0.03 | −38.1 ± 2.0 | −3.00 ± 0.06 |
| $ClO_4^-$ | −64.6 ± 1.2 | −1.40 ± 0.06 | −46.9 ± 1.6 | 0.20 ± 0.05 | −54.2 ± 1.6 | −1.34 ± 0.04 |
| $NO_2^-$ | −58.4 ± 1.5 | 0.25 ± 0.04 | −55.8 ± 1.5 | 0.35 ± 0.02 | −58.4 ± 1.5 | 0.10 ± 0.03 |
| $SCN^-$ | −91.5 ± 1.6 | 0.90 ± 0.03 | −60.2 ± 1.3 | 0.80 ± 0.06 | −60.6 ± 1.3 | 0.75 ± 0.02 |
| $Cl^-$ | −91.7 ± 0.7 | 0 | −60.5 ± 0.5 | 0 | −60.1 ± 0.5 | 0 |

$_a$ Selectivity coefficients are not reliable if the indicated electrode slopes are non-Nernstian The potentiometric anion selectivity is obviously improved in the presence of a cation exchanger, which suggests a charged carrier mechanism for the grafted ionophore. Hence, the basic mechanism for the anion recognition equilibrium appears to be unaltered upon covalent attachment.

The selectivities of the membranes with grafted In(HEPEAC)Cl were found to be similar to the membranes containing free ionophores. However, the grafted ionophore-based membranes showed Nernstian slopes toward chloride, nitrite, and thiocyanate ions, which indicates that dimerization reactions cannot occur due to the covalent immobilization of the ionophore.

Response and recover times were also greatly enhanced with membranes containing grafted, rather than free ionophore, with typical response times of 10 s and a recovery time in the background buffer of 40 s, relative to about 8 min and more than 26 min for membranes with free In(HEPEAC)Cl.

To investigate the possible influence from the difference in the membrane matrixes, the membrane containing free In(HEPEAC)Cl ionophores, PVC/NPOE, and 20 wt % blank MMA-DMA was prepared. The response slopes and selectivity of such membranes are shown in Table 2. The super-Nernstian slopes for $Cl^-$, $ClO_4^-$, and $SCN^-$ indicated that the simple blending of two different matrixes has no effect on the dimerization process and dimer formation can only be prevented through covalent attachment.

EXAMPLE 8

It was reported that ISE membranes containing In(OEP)Cl in a polyurethane matrix also showed Nernstian response slopes to chloride although super-Nernstian responses to more strongly responding anions were still observed. With absorbance experiments, dimerization was still found to occur, although the extent of dimerization decreased with decreasing chloride concentration in the contacting sample. (23)

As reported earlier, the UV/visible absorbance band of the metalloporphyrin around 390 nm correlates to the dimer, while the band at ~410 nm originates from the monomeric porphyrin. (23,31) The absorbance spectra of PVC-NPOE membranes containing free and covalently grafted indium porphyrins in addition to NaTFPB were here compared to confirm that no dimerization occurs in membranes with covalently attached ionophores.

Figure 5:
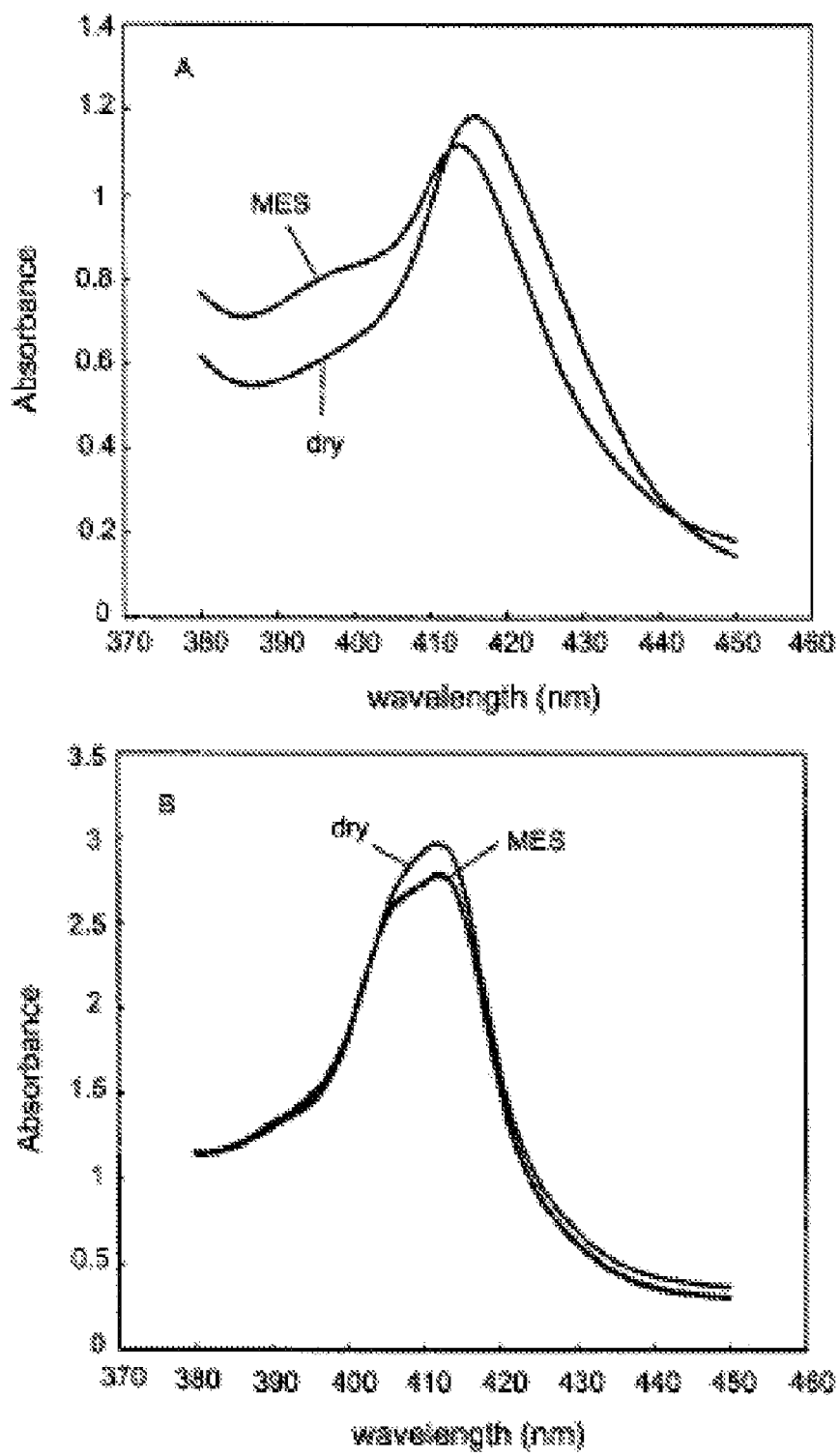
FIG. 5 shows the UV/visible spectra of thin films containing free (A) and grafted (B) In (HEPEAC)Cl ionophore and 30 mol % NaTFPB upon exposure to 0.05 M MES buffer at pH 5.5, wherein dimer formation is only visible in (A)

As illustrated in FIG. 5A, the dry NPOE film containing free In(HEPEAC)Cl shows a Soret band at 415 nm, indicative of the undimerized monomeric species. After 10-min exposure to MES buffer at pH 5.5, a new Soret band appears at 395 nm, indicating the presence of hydroxide-bridged porphyrin dimers. At the same time, a decrease of the monomeric peak at 415 nm is observed.

In contrast, no dimer peak is visible at 390 nm for the PVC-NPOE membrane containing the grafted ionophore, even after soaking for 30 min (see FIG. 5B). The slight change in the spectrum at 410 nm is probably due to the exchange of $Cl^-$ and $OH^-$ as axial ligand for In (III). (23) These results support the notion that a covalent attachment prevents the dimerization of the indium porphyrin ionophores in polymeric membranes.

Figure 6:
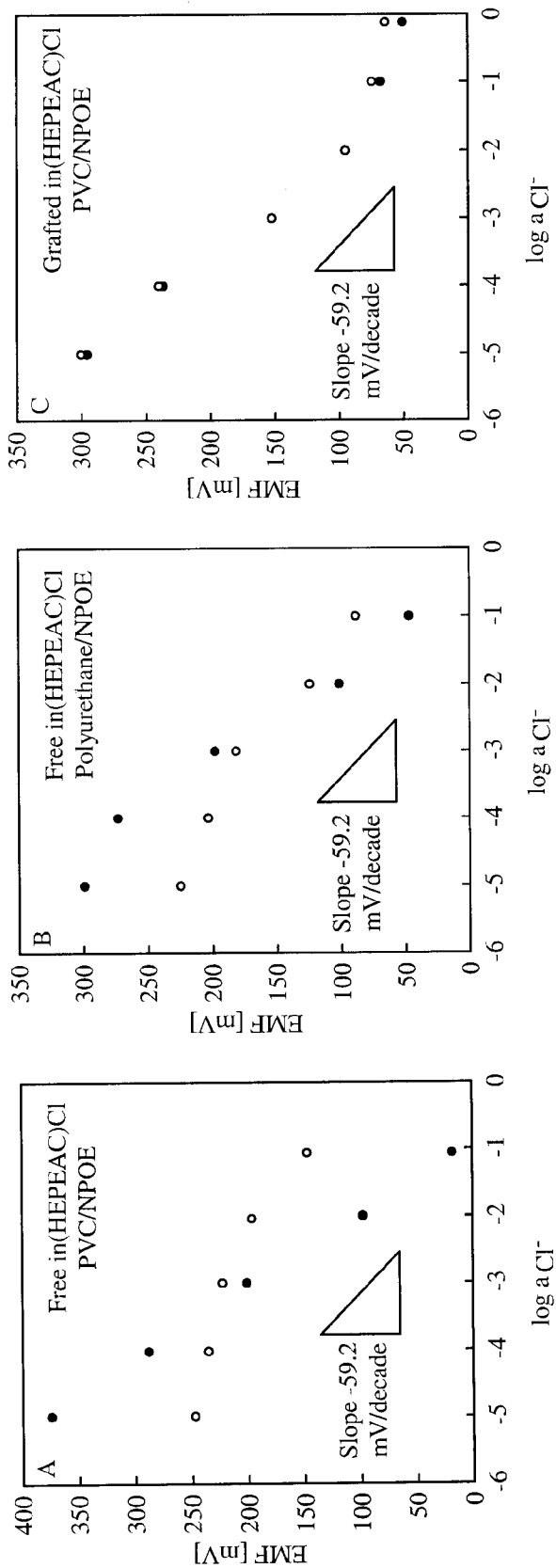
FIG. 6 shows the lifetime behavior of chloride-selective membranes, in continuous contact with 0.01 M NaCl, containing free In (HEPEAC)Cl in PVC-NPOE (A) and polyurethane membranes (B) after 1 day (filled circles) and 5 days (open circles), and containing grafted In (HEPEAC)Cl-MMA-DMA (20 wt %) in PVC-NPOE (C) after 1 day (filled circles) and 6 weeks (open circles).

To further compare the polyurethane membrane with copolymer membrane, the chloride response curves of polyurethane membrane with free In(HEPEAC)Cl were recorded (FIG. 6B). The initial super-Nernstian slopes—79.4 mV decade$^{-1}$) indicated that the polyurethane matrix cannot weaken the formation of the dimers in the membrane for this ionophore. The response properties of indium porphyrin-based ISEs cannot simply be improved by changing the polymer matrix.

EXAMPLE 9

The lifetime of indium porphyrin-based ISEs and optodes is usually quite short since the dimers have a poor solubility in NPOE or DOS plasticized polymeric membranes. Consequently, the dimeric species crystallizes quickly. (36) In our experience, ISE membranes containing free indium porphyrin ionophores can only be used for a few days if kept in contact with solution. It was reported that In(OEP)Cl crystallizes in optode films after soaking in pH 5.5 MES buffer with $10^{-3}$ M NaCl for 4 h, although fresh optode films can be stored dry for at least one week and subsequently maintain good chloride response.

The lifetimes of free In(HEPEAC)Cl ionophore-based ISE membranes with different polymer matrixes, PVC (FIG. 6A) and polyurethane (FIG. 6B) were studied. Both membranes exhibited a super-Nernstian response slope to chloride ions and the membranes showed drastically reduced slopes and selectivities after 5 days of conditioning in 0.01 M NaCl solution.

For membranes containing the grafted indium porphyrin ionophore, we expected a much longer lifetime since dimer formation is suppressed. Indeed, membranes with grafted ionophore still showed Nernstian slopes and good selectivities after six weeks soaking in 0.01 M NaCl solution as shown in FIG. 6C and Table 3. Plasticizer-free MMA-DMA membranes containing covalently attached indium porphyrin ionophores were not tested here because the reduced mechanical robustness currently limits the lifetime of the resulting ISE membranes to 2-3 days.

TABLE 3

Electrode Slopes and Logarithmic Selectivity Coefficients'$^a$ of Grafted In(HEPEAC)Cl-Based PVC-NPOE Membranes after 6 Weeks Stored in 0.01 M NaCl

| | no NaTFPB | | 30 mol % NaTFPB | |
|---|---|---|---|---|
| ions | slope | log $K_{Cl,I}^{pot}$ | Slope | log $K_{Cl,I}^{pot}$ |
| $NO_3^-$ | −12.8 ± 2.0 | −2.19 ± 0.08 | −35.7 ± 2.0 | −3.03 ± 0.03 |
| $ClO_4^-$ | −45.2 ± 1.6 | 0.16 ± 0.08 | −54.4 ± 0.8 | −1.37 ± 0.04 |
| $NO_2^-$ | −53.6 ± 1.3 | 0.12 ± 0.10 | −59.4 ± 1.5 | 0.04 ± 0.03 |
| $SCN^-$ | −58.1 ± 1.3 | 0.78 ± 0.12 | −58.8 ± 1.1 | 0.48 ± 0.03 |
| $Cl^-$ | −59.3 ± 0.6 | 0 | −59.7 ± 0.4 | 0 |

$^a$ Selectivity coefficients are not reliable if the indicated electrode slopes are non-Nernstian.

Membranes based on the covalently grafted indium porphyrins exhibited a lower upper detection limit in comparison to free ionophore-based membranes. In NaCl solutions, the logarithmic upper detection limit was ~−0.5, while in KCl samples, it was ~−1.8 (data not shown). The lower detection limit found in KCl indicates that the grafted indium porphyrin exhibits a stronger apparent complexation with chloride ions than the ungrafted ionophore. It is well established that the upper detection limit is ordinarily dictated by massive coextraction of analyte ion and its counterion into the membrane. The stronger apparent complexation can be rationalized on the basis of the reduced dimer formation with the grafted ionophore. The dimerization reaction reduces the concentration of uncomplexed ionophore in the membrane, which effectively weakens the overall complexation equilibrium of chloride ions. If this dimerization equilibrium is suppressed, a stronger apparent complexation should result, leading to a lower upper detection limit. The lower detection limit of these chloride-selective electrodes was not the principal focus of this work because of the high abundance of chloride in most samples. It is anticipated, however, that the lower detection limit will be strongly dependent on the sample pH because of the limited discrimination of hydroxide ions, in analogy to other systems recently studied. $_{(24)}$

EXAMPLE 10

In(AOTPP)Cl (see FIG. 1), a polymerizable derivative of indium$^{III}$tetraphenylporphyrin chloride (In(TPP)Cl), was taken as an alternative example to evaluate the effect of covalent attachment. It was reported in the literature that membranes containing In(TPP)Cl show a selectivity pattern that deviates from those with the indium$^{III}$octaethylporphyrin discussed above. Indeed, In(TPP)Cl-based membranes were proposed as nitrite-selective membranes. $_{(6,12)}$ The response slopes and selectivities for membranes containing In(AOTPP)Cl are summarized in Table 4.

TABLE 4

Potentiometric Responses of Free and Covalently Grafted Nitrite-Selective In(AOTPP)Cl-Based PVC-NPOE Membranes Containing 30 mol % NaTFPVB$^a$

| | free In(AOTPP)Cl | | grafted In(AOTPP)Cl | | In(TPP)Cl |
|---|---|---|---|---|---|
| ion J | slope | log $K_{Cl,J}^{pnt}{}_a$ | slope | log $K_{Cl,J}^{pnt}$ | log $K_{Cl,J}^{pnt}$ |
| Cl$^-$ | −58.1 ± 1.0 | −0.58 ± 0.04 | −52.7 ± 1.2 | −0.40 ± 0.03 | −1.20 |
| ClO$_4^-$ | −45.6 ± 1.1 | −2.71 ± 0.06 | −46.2 ± 0.8 | −2.07 ± 0.02 | −2.43 |
| NO$_3^-$ | −38.8 ± 0.6 | −3.18 ± 0.03 | −35.2 ± 1.0 | −2.80 ± 0.04 | −2.65 |
| SCN$^-$ | −81.5 ± 1.2 | 0.32 ± 0.02 | −60.4 ± 0.8 | 0.21 ± 0.02 | −1.0 |
| NO$_2^-$ | −70.2 ± 0.8 | 0 | −58.7 ± 0.6 | 0 | 0 |

$_a$ Selectivity coefficients are not reliable if the indicated electrode slopes are non-Nernstian.

As with the In(OEP)Cl systems discussed above, membranes containing free ionophore in PVC-NPOE membranes showed a super-Nernstian response slope to nitrite and thiocyanate anions. The selectivity of membranes containing free In(AOTPP)Cl is somewhat inferior to that of membranes containing In(TPP)Cl, especially over SCN$^-$ and Cl$^-$. The discrimination of the lipophilic anions nitrate and perchlorate is, however, excellent. In contrast to the membranes containing free In(AOTPP)Cl, the membranes with grafted In-(AOTPP)Cl-MMA-DMA now showed Nernstian response slopes to nitrite and thiocyanate ions as shown in Table 4. The numerical selectivity coefficients are comparable to membranes containing the free ionophore. It should be kept in mind, however, that theoretical response slopes are used for the calculation of selectivity coefficients on the basis of the Nicolsky equation. In fact, selectivity coefficients are obtained by dividing the potential difference for two separately measured ions at 1 M activities by the theoretical slope for the primary ion. $_{(4)}$ Selectivity values obtained with membranes containing drastically super-Nernstian slopes are therefore not strictly meaningful and are expected to indicate a larger than realistic selectivity. The fact that membranes containing covalently attached indium$^{III}$ porphyrins showed essentially unaltered selectivity coefficients over membranes with free ionophores is therefore a welcome finding.

CONCLUSIONS

A chemical attachment method for indium$^{III}$porphyrin ionophores was used to prepare ISE membranes that show Nernstian response slopes. The ionophores are covalently attached, which prevents the formation of the dimeric species in the membranes. The covalent attachment does not alter the apparent selectivity of the resulting membranes, which is a welcome result considering the change in the response slope. The lifetime of the ISEs was found to be much improved upon covalent attachment of the ionophores, not simply because leaching is eliminated but because the crystallization of the indium porphyrin was avoided. The only drawback found with membranes containing the grafted In$^{III}$(HEPEAC)Cl was the reduced upper detection limit, which was attributed to a stronger effective stabilization of chloride by the ionophore.

Having thus described the invention, it should be apparent that numerous modifications and adaptations may be resorted to without departing from the scope and fair meaning of the instant invention as set forth hereinabove and as described hereinbelow by the claims.

Although the present invention has been described in considerable detail with reference to certain preferred versions thereof, other versions are possible. Therefore, the spirit and scope of the appended claims should not be limited to the description of the preferred versions described herein.

All features disclosed in the specification, including the claims, abstracts, and drawings, and all the steps in any method or process disclosed, may be combined in any combination, except combinations where at least some of such features and/or steps are mutually exclusive. Each feature disclosed in the specification, including the claims, abstract, and drawings, can be replaced by alternative features serving the same, equivalent or similar purpose, unless expressly stated otherwise. Thus, unless expressly stated otherwise, each feature disclosed is one example only of a generic series of equivalent or similar features.

Any element in a claim that does not explicitly state "means" for performing a specified function or "step" for performing a specified function, should not be interpreted as a "means" or "step" clause as specified in 35 U.S.C. § 112.

BIBLIOGRAPHY

The following references are each incorporated herein by reference:

(1) Amemiya, S.; Buhlmann, P.; Odashima, K. *Anal. Chem.* 2003, 75, 3329.
(2) Ammann, D.; Huser, M.; Krautler, B.; Rusterholz, B.; Schulthess, P.; Lindemann, B.; Haider, E.; Simon, W. *Helv. Chim. Acta* 1986, 69, 849.
(3) Bakker, E.; Malinowska, E.; Schaller, R. D.; Meyerhoff, M. E. *Talanta* 1994, 41, 881.
(4) Bakker. E.; Pretsch, E.; Buhlmann, P. *Anal. Chem.* 2000, 72, 1127.

(5) Brasuel, M.; Kopelman, R.; Miller, T. J.; Tjalkens, R.; Philbert, M. A. *Anal. Chem.* 2001, 73, 2221.
(6) Buhlmann, P.; Pretsch, E.; Bakker, E. *Chem. Rev.* 1998, 98. 1593.
(7) Byrne, C. J.; Ward, A. D. *Tetrahedron Lett.* 1988, 29, 1421.
(8) Chaniotakis, N. A.; Chasser, A. M; Meyerhoff, M. E.; Goves, J. T. *Anal. Chem.* 1988, 60, 185.
(9) Chaniotakis, N. A.; Park, S. B.; Meyerhoff, M. E. *Anal. Chem.* 1989, 61, 566.
(10) Coutant, D. E.; Clarke, S. A.; Francis, A. H.; Meyerhoff, M. E. *J. Chromatogr., A* 1998, 824, 147.
(11) Eaton, S. S.; Eaton, G. R. *J. Am. Chem. Soc.* 1975, 97, 3660
(12) Gao. D.: Gu, J.; Yu, R. Q.; Zheng, G.-D. *Analyst* 1995, 120, 499
(13) Gorski, L.; Malinowska, E.; Parzuchowski, P.; Zhang, W.; Meyerhoff, M. E. *Electroanalysis* 2003, 15, 1229.
(14) Heng, L. Y.; Hall, E. A. H. *Anal. Chem.* 2000, 72, 42.
(15) Heng, L. Y.; Hall, E. A. H. *Electroanalysis* 2000, 12, 178.
(16) Hodinar, A.; Jyo, A. *Chem. Lett.* 1988, 993.
(17) Huser, M.; Morf, W. E.; Fluri, K.; Seiler, K.: Schulthess, P.; Simon, W. *Helv. Chim. Acta* 1990, 73, 1481.
(18) Jyo, A.; Egawa, H. *Anal. Sci.* 1992, 8, 823.
(19) Kamachi, M.; Akimoto, H.; Nozakura, S. *J. Polym. Sci. Polym. Lett. Ed* 1983, 21, 693.
(20) Kibbey, C. E.; Park, S. B.; Deadwyler, G.; Meyerhoff, M. E. *J. Electroanal. Chem.* 1991, 335, 135.
(21) Li, X.; Harrison, D. J. *Anal. Chem.* 1991, 63, 2168.
(22) Malinowska, E.; Gawart, L.; Parzuchowski, P.; Rokicki, G.; Brzozka, Z. *Anal. Chim. Acta* 2000, 421, 93.
(23) Malinowska, E.: Niedziolka, J.; Meyerhoff, M. E. *Anal. Chim. Acta* 2001, 432, 67.
(24) Malon, A.; Radu, A.; Qin, W.; Qin, Y.; Ceresa, A.; Maj-Zurawska, M.; Bakker, E.; Pretsch, E. *Anal. Chem.* 2003, 75, 3865.
(25) Park, S. B.; Matuszewski, W.; Meyerhoff, M. E.; Liu, Y. H.; Kadish, K. M. *Electroanalysis* 1991, 3, 909.
(26) Phadke, A. S.; Morgan, A. R. *Tetrahedron Lett.* 1993, 34, 1725.
(27) Qin, Y.; Peper, S.; Radu, A.; Ceresa, A.; Bakker, E. *Anal. Chem.* 2003, 75, 3038.
(28) Qin, Y.; Peper, S.; Bakker, E. *Electroanalysis* 2002, 14, 1375.
(29) Retter, R.; Peper, S.; Bell, M.; Tsagkatakis, I.; Bakker, E. *Anal. Chem.* 2002, 74, 5420.
(30) Schaller, U.; Bakker, E.; Spichiger, U. E.; Pretsch, E. *Anal. Chem* 1994, 66, 391 (31) Steinle, E. D.; Amemiya, S.; Buhlmann, P.; Meyerhoff, M. E. *Anal. Chem.* 2000, 72, 5766.
(32) Steinle, E. D.; Schaller, U.; Meyerhoff, M. E. *Anal. Sci.* 1998, 14, 79.
(33) Telting-Diaz, M.; Bakker, E. *Anal. Chem.* 2002, 74, 5251.
(34) Tsagkatakis, I.; Peper, S.; Bakker, E. *Anal. Chem.* 2001, 73, 6083.
(35) Yoon, I. J.; Shin, J. H.; Paeng, 1. R.; Nam, H.; Cha, G. S.; Paeng, K.-J. *Anal. Chim. Acta* 1998, 367, 175.
(36) Zhang, W.; Rozniecka, E.; Malinowska, E.; Parzuchowski, P.; Meyerhoff, M. E. *Anal. Chem.* 2002, 74, 4548.

What is claimed is:

1. A graft copolymer having selectivity for a target anion, the graft copolymer comprising co-polymerized units of:
    a. a functionalized ionophore monomer comprising a metalloporphyrin, a polymerizable group; and a spacer joining the metalloporphyrin and the polymerizable group; and
    b. a co-monomer, which co-polymerizes with the functionalized ionophore monomer, wherein at least a portion of the functionalized ionophore is covalently attached to the copolymer in a manner preventing formation of metalloporphyrin dimers.

2. The graft copolymer of claim 1, wherein formation of metalloporphyrin dimers is eliminated.

3. The graft copolymer of claim 1, having selectivity for a target anion selected from the group consisting of chloride, salicylate, thiocyanate, and nitrite.

4. The graft copolymer of claim 1, wherein the metalloporphyrin is an In (III), Mn(III), Sn(IV), Ru(II), or CO(III) porphyrin.

5. The graft copolymer of claim 1, wherein the polymerizable group of the functionalized ionophore monomer is an acrylic or methacrylic group.

6. The graft copolymer of claim 1, wherein the spacer is an oxyalkyl or oxyphenyl group.

7. The graft copolymer of claim 1, wherein the functionalized ionophore monomer is chloro(3-[18-(3-acryloyloxypropyl)-7,12-bis(1-methoxyethyl)-3,8,13,17-tetramethylporphyrin-2-yl]-propyl ester) indium (III).

8. The graft copolymer of claim 1, wherein the functionalized ionophore monomer is chloro(5-(4-acryloyloxyphenyl)-10,15,20-triphenylporphyrinato) indium (III).

9. The graft copolymer of claim 1, wherein the co-monomer is selected from the group consisting of acrylates and methacrylates.

10. The graft copolymer of claim 1, wherein the co-monomer comprises methyl methacrylate and decyl methacrylate.

11. The graft copolymer of claim 1, containing sufficient polymerized units of co-monomer to prevent formation of metalloporphyrin dimers.

12. A graft copolymer having selectivity for chloride ions, the graft copolymer comprising co-polymerized units of:
    a. a functionalized ionophore monomer comprising an indium porphyrin, a polymerizable group and a spacer joining the indium porphyrin and the polymerizable group; and
    b. a methacrylate co-monomer, which co-polymerizes with the functionalized ionophore monomer, wherein at least a portion of the functionalized ionophore is covalently attached to the copolymer in a manner preventing formation of matalloporphyrin dimers.

13. The graft copolymer of claim 12, containing the functionalized ionophore monomer in an amount of about one to five percent by weight.

14. The graft copolymer of claim 12, wherein the methacrylate co-monomer is methyl methacrylate and decyl methacrylate.

15. The graft copolymer of claim 12, containing no metalloporphyrin dimers.

16. A graft copolymer having selectivity for a target anion, the graft copolymer comprising co-polymerized units of:
    a. a functionalized ionophore monomer comprising a metalloporphyrin, a polymerizable group and a spacer joining the metalloporphyrin and the polymerizable group, wherein the functionalized ionophore monomer is chloro(3-[18-(3 -acryloyloxypropyl)-7,12-bis(1-methoxyethyl)-3,8,13,17-tetramethylporphyrin-2-yl]-propyl ester) indium (III); and
    b. a co-monomer, which co-polymerizes with the functionalized ionophore monomer, wherein at least a portion of the functionalized ionophore is covalently attached to the copolymer in a manner preventing formation of metalloporphyrin dimers.

17. A graft copolymer having selectivity for a target anion, the graft copolymer comprising co-polymerized units of:
  a. a functionalized ionophore monomer comprising a metalloporphyrin, a polymerizable group and a spacer joining the metalloporphyrin and the polymerizable group, wherein the functionalized ionophore monomer is chloro(5-(4-acryloyloxyphenyl)-10,15,20-triphenylporphyrinato) indium (III); and
  b. a co-monomer, which co-polymerizes with the functionalized ionophore monomer, wherein at least a portion of the functionalized ionophore is covalently attached to the copolymer in a manner preventing formation of metalloporphyrin dimers.

* * * * *

UNITED STATES PATENT AND TRADEMARK OFFICE
CERTIFICATE OF CORRECTION

PATENT NO.         : 7,678,252 B2
APPLICATION NO.    : 11/424185
DATED              : March 16, 2010
INVENTOR(S)        : Eric Bakker and Yu Qin It is certified that error appears in the above-identified patent and that said Letters Patent is hereby corrected as shown below:

At column 1, line 20, please replace "fights" with -- rights -- so that the corresponding phrase reads -- certain rights in the invention --.

At column 17, line 65, Claim 1, please remove ";" so that the corresponding phrase reads -- a polymerizable group and a spacer --.

Signed and Sealed this

Fourth Day of May, 2010

David J. Kappos
*Director of the United States Patent and Trademark Office*